United States Patent
Kruspe (12)

(10) Patent No.: US 6,326,785 B1
(45) Date of Patent: Dec. 4, 2001

(54) NUCLEAR MAGNETIC RESONANCE TOOL WITH MAGNETOSTRICTIVE NOISE COMPENSATION

(75) Inventor: Thomas Kruspe, Halber Weg (DE)

(73) Assignee: Baker Hughes, Inc., Houston, TX (US)

( * ) Notice: Subject to any disclaimer, the term of this patent is extended or adjusted under 35 U.S.C. 154(b) by 0 days.

(21) Appl. No.: 09/618,851

(22) Filed: Jul. 18, 2000

(51) Int. Cl.[7] .................................................. G01V 3/00
(52) U.S. Cl. ........................................ 324/303; 324/300
(58) Field of Search .................................. 324/303, 300, 324/318, 244

(56) References Cited

U.S. PATENT DOCUMENTS

| 4,350,955 | 9/1982 | Jackson et al. ................. 324/303 |
| 4,433,291 | * 2/1984 | Yariv ............................... 324/244 |
| 5,712,566 | 1/1998 | Taicher et al. .................. 324/303 |
| 6,215,304 | * 4/2001 | Slade ............................... 324/303 |

FOREIGN PATENT DOCUMENTS

| 2141236 | 12/1984 | (GB) . |
| 0932055A2 | 7/1999 | (GB) . |

* cited by examiner

Primary Examiner—Jay Patidar
(74) Attorney, Agent, or Firm—Madan, Mossman & Sriram, PC (57) ABSTRACT

An NMR logging apparatus and method are provided including an antenna having compensation for magnetostrictive ringing. The antenna comprises at least one inductive winding and a core having a first portion having positive magnetostriction in the presence of a radio frequency magnetic field, and a second portion having negative magnetostriction in the presence of the radio frequency magnetic field. The positive and negative portions may be tiles shaped as polygonal cylinders arranged with alternating positive and negative tiles forming at least one layer of a matrix, or the portions may be constructed using ferrite powder fixed in epoxy and shaped in polygonal cylinders.

27 Claims, 5 Drawing Sheets

NUCLEAR MAGNETIC RESONANCE TOOL WITH MAGNETOSTRICTIVE NOISE COMPENSATION

BACKGROUND OF THE INVENTION

1. Field of the Invention

The present invention relates to oil well drilling tools. In particular, the present invention relates to nuclear magnetic resonance measurement while drilling tools.

2. Description of the Related Art

In the oil and gas industry, hydrocarbons are recovered from formations containing oil and gas by drilling a borehole to the formation using a drilling system. The system typically comprises a drill bit carried at an end of a drill string. The drill string is comprised of a tubing which may be drill pipe made of jointed sections or a continuous coiled tubing and a drilling assembly that has a drill bit at its bottom end. The drilling assembly is attached to the bottom end of the tubing. To drill a well bore, a mud motor carried by the drilling assembly rotates the drill bit, or the bit is coupled to drill pipe, which is rotated by surface motors. A drilling fluid, also referred to as "mud," is pumped under pressure from a source at the surface (mud pit) through the tubing. The mud serves a variety of purposes. It is designed to provide the hydrostatic pressure that is greater than the formation pressure to avoid blowouts. The mud drives the drilling motor (when used) and it also provides lubrication to various elements of the drill string.

The mud flowing in the annular space between the drill string and borehole wall will invade the formation for a short distance due to the pressure exerted by the mud. Although this increased pressure helps prevent blowouts, the region, known as the invasion or invaded zone, becomes contaminated with the mud. Any measurements on formation fluids within the invasion zone may be inaccurate because of the contamination. For this reason, it is desirable to sample and test fluids beyond the invaded zone.

During drilling operations, information on a specific formation is gathered once the borehole reaches the area known as the zone of interest. Downhole instruments and/or sampling devices are utilized at the zone of interest to gather data regarding various parameters of interest including pressure, temperature and other physical and chemical properties of the formation fluid and or mud. These data-gathering operations during drilling are known as measurement while drilling (MWD) or logging while drilling (LWD). The differences between MWD and LWD are known in the art and are not particularly relevant to the present invention. Therefore, the focus will be limited to LWD terminology. The intent, however, is to include MWD, along with wireline logging, embodiments and methods within the scope of the present invention.

One LWD method used to determine characteristics of formation fluid is known as nuclear magnetic resonance or NMR well logging. NMR well logging instruments can be used for determining properties of earth formations including the fractional volume of pore space and the fractional volume of mobile fluid filling the pore spaces of the earth formations. Methods of using NMR measurements for determining the fractional volume of pore space and the fractional volume of mobile fluid are described, for example, in Spin Echo Magnetic Resonance Logging: Porosity and Free Fluid Index Determination, M. N. Miller et al, Society of Petroleum Engineers paper no. 20561, Richardson, Tex., 1990.

An NMR log is dependent on the alignment of the magnetic moment of protons with an impressed magnetic field. In NMR logging applications, the protons of hydrogen nuclei are of interest. The spins of protons tend to align themselves with the magnetic field. NMR instruments typically make measurements corresponding to an amount of time for hydrogen nuclei present in the earth formations to substantially realign their spin axes, and consequently their bulk magnetization, with an applied magnetic field. The applied magnetic field is typically provided by a permanent magnet disposed in the instrument. The spin axes of hydrogen nuclei in the earth formation, in the aggregate, align with the magnetic field applied by the magnet.

The NMR instrument also typically includes an antenna, positioned near the magnet and shaped so that a pulse of RF power conducted through the antenna induces an RF magnetic field in the earth formation. The RF magnetic field is generally orthogonal (perpendicular) to the field applied by the magnet. The first RF pulse, typically called a 90-degree pulse, has a duration and amplitude predetermined so that the spin axes of the hydrogen nuclei generally align themselves perpendicularly to the static magnetic field applied by the magnet. After the 90 degree pulse ends, the nuclear magnetic moments of the hydrogen nuclei gradually "relax" or return in a precessional rotation to their original alignment with the field of the magnet. The amount of time taken for this relaxation is related to petrophysical properties of interest of the earth formation.

The precessional rotation generates RF energy at a frequency proportional to the strength of the magnetic field applied by the magnet, this frequency being referred to as the Larmor frequency. The constant of proportionality for the Larmor frequency is known as the gyromagnetic ratio ($\gamma_0$). The gyromagnetic ratio is unique for each different chemical elemental isotope. The spin axes of the hydrogen nuclei gradually "dephase" because of inhomogeneities in the magnet's field and because of differences in the chemical and magnetic environment within the earth formation. Dephasing results in a rapid decrease in the magnitude of the voltages induced in the antenna. The rapid decrease in the induced voltage is referred to as the free induction decay (FID). The FID decay rate is mainly determined by the spin dephasing caused by static magnetic field inhomogeneities. A process referred to as spin-echo measurement can substantially reestablish the spin decay in a non-homogeneous field.

Spin echo measurement can be described as in the following discussion. After a predetermined time period following the FID, another RF pulse is applied to the antenna. This RF pulse has predetermined amplitude and duration to realign the spin axes of the hydrogen nuclei in the earth formation by an axial rotation of 180 degrees from their immediately previous orientations, and is therefore referred to as a 180-degree pulse. After the end of the 180-degree pulse, hydrogen nuclear axes that were precessing at a slower rate are then positioned so that they are "ahead" of the faster precessing spin axes. The 180-degree reorientation of the nuclear spin axes therefore causes the faster precessing axes to be reoriented "behind" the slower precessing axes. The faster precessing axes then eventually "catch up" to, and come into approximate alignment with, the slower precessing axes after the 180-degree reorientation. As a large number of the spin axes thus become "rephased" with each other, the hydrogen nuclear axial precessions are again able to induce measurable voltages in the antenna. The voltages induced as a result of the rephasing of the hydrogen nuclear axes with each other after a 180-degree pulse are referred to as a "spin echo".

The spin echo induced voltage is typically smaller than the original voltage generated after cessation of the first RF pulse, because the aggregate nuclear axial alignment, and consequently the bulk magnetization, of the hydrogen nuclei at the time of the spin echo is at least partially realigned with the magnet's field and away from the sensitive axis of the antenna. The spin echo voltage itself decays by FID as the faster precessing nuclear axes quickly "dephase" from the slower precessing nuclear axes.

After another period of time, typically equal to two of the predetermined time periods between the initial 90-degree RF pulse and the 180-degree pulse, another RF pulse of substantially the same amplitude and duration as the 180-degree pulse is applied to the antenna. This subsequent RF pulse causes another 180-degree rotation of the spin axis orientation. This next 180-degree pulse, and the consequent spin axis realignment again causes the slower precessing spin axes to be positioned ahead of the faster precessing spin axes. Eventually another spin echo will occur and induce measurable voltages in the antenna. The induced voltages of this next spin echo will typically be smaller in amplitude than those of the previous spin echo.

Successive 180-degree RF pulses are applied to the antenna to generate successive spin echoes, each one typically having a smaller amplitude than the previous spin echo. The rate at which the peak amplitude of the spin echoes decays is related to petrophysical properties of interest of the earth formations. A certain number of spin echoes needed to determine the rate of spin echo amplitude decay is related to the properties of the earth formation; in some cases as many as 1,000 spin echoes may be needed to determine the amplitude decay corresponding to the properties of the earth formation which are of interest. The distribution of rates at which the peak amplitude of the spin echoes decay is directly related to parameters of interest in the earth formation.

As previously stated, NMR tools use an antenna for creating the RF field and for receiving the echo signal from the formation fluid being analyzed. An NMR antenna comprises typically a coil disposed around a core for increasing the inductance of the coil and to minimize eddy currents in the steel tool housing. The use of an intensifying core allows for a smaller antenna, which is particularly useful in downhole applications.

High-gain amplifiers are utilized to amplify low power echoes received prior to processing the signal. It is very important that the echo is distinguishable over noise. The ratio of signal amplitude to the noise amplitude, known as the signal to noise ratio, should be as high as possible. This will ensure that the echo can be distinguished even after amplification.

A primary source of noise known as ring-down is induced by mechanical oscillations within the antenna and other components of the sensor. A major cause of the oscillation is a certain characteristic of the antenna core material usually selected from a soft ferrite. Ferrite is a material that changes shape when in the presence of a magnetic field. The material then returns to the original shape when the magnetic field is removed. This property is known as magnetostriction. The ringing generated by magnetostriction is termed magnetostrictive ringing. From investigations of ferrite materials, it is known that the different materials exhibit different deformation characteristics when exposed to the same magnetic field. Some ferrites expand, while others contract with an applied field. Both types, as stated, return to the original dimensions when the field is removed.

One type of NMR well logging apparatus is described, for example in U.S. Pat. No. 4,350,955 issued to Jackson et al. The apparatus disclosed in the Jackson et al '955 patent includes permanent magnets configured to induce a magnetic field in the earth formations, which has a toroidal volume of substantially uniform magnetic field strength. This patent describes very well the physics of NMR technology and is hereby incorporated by reference.

An apparatus disclosed in U.K. patent application no, 2,141,236 filed by Clow et al and published on Dec. 12, 1984 provides improved signal-to-noise ratio when compared with the apparatus of Jackson et al '955 by including a high magnetic permeability ferrite in the antenna.

Another NMR well logging apparatus is described, for example in U.S. Pat. No. 4,710,713 issued to Taicher et al. The apparatus disclosed in the Taicher et al '713 patent includes a substantially cylindrical permanent magnet assembly which induces a static magnetic field having substantially uniform field strength within an annular cylindrical volume.

The apparatus disclosed in the Taicher et al '713 patent is especially subject to magnetoacoustic and magnetostrictive parasitic signals or "ringing". First, because the antenna is located within the strongest part of the magnet's field, when RF electrical pulses are applied to the antenna acoustic waves can be generated in the antenna by an effect known as the "Lorenz force". The antenna returns to its original shape in a series of damped mechanical oscillations in a process referred to as "magnetoacoustic ringing". Ringing can induce large voltages in the antenna which interfere with the measurement of the voltages induced by the NMR spin echoes. Additionally, the magnet is located in the highest strength portion of the RF magnetic field. The magnet can be deformed by magnetostriction. When each RF power pulse ends, the magnet tends to return to its original shape creating the magnetostrictive ringing as described above, which as magnetoacoustic ringing, can induce large voltages in the antenna making it difficult to measure the spin echoes.

Another NMR logging tool is described in U.S. Pat. No. 5,712,566 issued to Taicher et al. The '566 patent points out the drawbacks of the above referenced patents including the adverse effects of magnetoacoustic and magnetostrictive ringing. The '566 patent teaches a restrictive configuration approach to the problem of ringing. The approach is to first configure the permanent magnet as a cylinder having an axial bore. The antenna rod (the soft ferrite material most subject to magnetostrictive ringing) is placed within the bore of the permanent magnet. This specific configuration places the sensor antenna in the pole of the permanent magnetic thereby substantially reducing magnetoacoustic ringing. The particular placement of the antenna within the bore also reduces magnetostrictive ringing by allowing substantially complete demagnetization of the ferrite rod during the dead period of the RF signal. However, ringing will still occur because the RF field induces a magnetic field that encircles the ferrite rod.

SUMMARY OF THE INVENTION

The present invention addresses some of the drawbacks described above by introducing the novel concept of a material matrix. A matrix of polygonal members comprised of oppositely characterized magnetostrictive materials forming a portion of an NMR tool will act upon itself thereby canceling the effect of magnetostriction in at least one direction. The overall result being reduced magnetostrictive ringing in the NMR tool.

The present invention provides an apparatus and a method for minimizing magnetostrictive ringing in a nuclear magnetic resonance measurement while drilling tool.

An antenna is provided comprising an inductive winding and a core for increasing inductance of the winding, the core further comprising a plurality of positive tiles shaped as polygonal cylinders exhibiting magnetostrictive properties characterized by expansion in certain directions in the presence of a magnetic field, and a plurality of negative tiles shaped as polygonal cylinders exhibiting magnetostrictive properties characterized by contraction in the same certain directions in the presence of the magnetic field, wherein the positive tile and the negative tiles are arranged with alternating positive and negative tiles forming at least one layer of a matrix.

Also provided is a nuclear magnetic resonance tool for analyzing a material is provided comprising a magnet for providing a first magnetic field substantially time invariant and at least partially encompassing a volume in which the material exists, an antenna for transmitting a second magnetic field in the radio frequency range substantially perpendicular to the first magnetic field, the antenna having at least one core section for increasing inductance, the at least one core section further comprising a plurality of tiles coupled such that tiles with opposing dimensional responses to a magnetic field are adjacent one another, and a receiver for sensing a signal emitted from the material.

Also provided is a method for analyzing formation fluids with an NMR tool, the method comprising conveying the tool into a well borehole on a wireline or drill string, creating a first magnetic field which is substantially time invariant beyond the borehole and invasion zone, and at least partially encompassing a volume in which the fluid exists, transmitting a second magnetic field in the radio frequency range substantially perpendicular to the first magnetic field with an antenna, the antenna having at least one core section for increasing inductance, the at least one core section further comprising a plurality of tiles coupled such that tiles with opposing dimensional responses to a magnetic field are adjacent one another, and sensing a signal emitted from the material with a receiver.

BRIEF DESCRIPTION OF THE DRAWINGS

For detailed understanding of the present invention, references should be made to the following detailed description of the preferred embodiment, taken in conjunction with the accompanying drawings, in which like elements have been given like numerals and wherein.

DESCRIPTION OF THE PREFERRED EMBODIMENT

Figure 1:
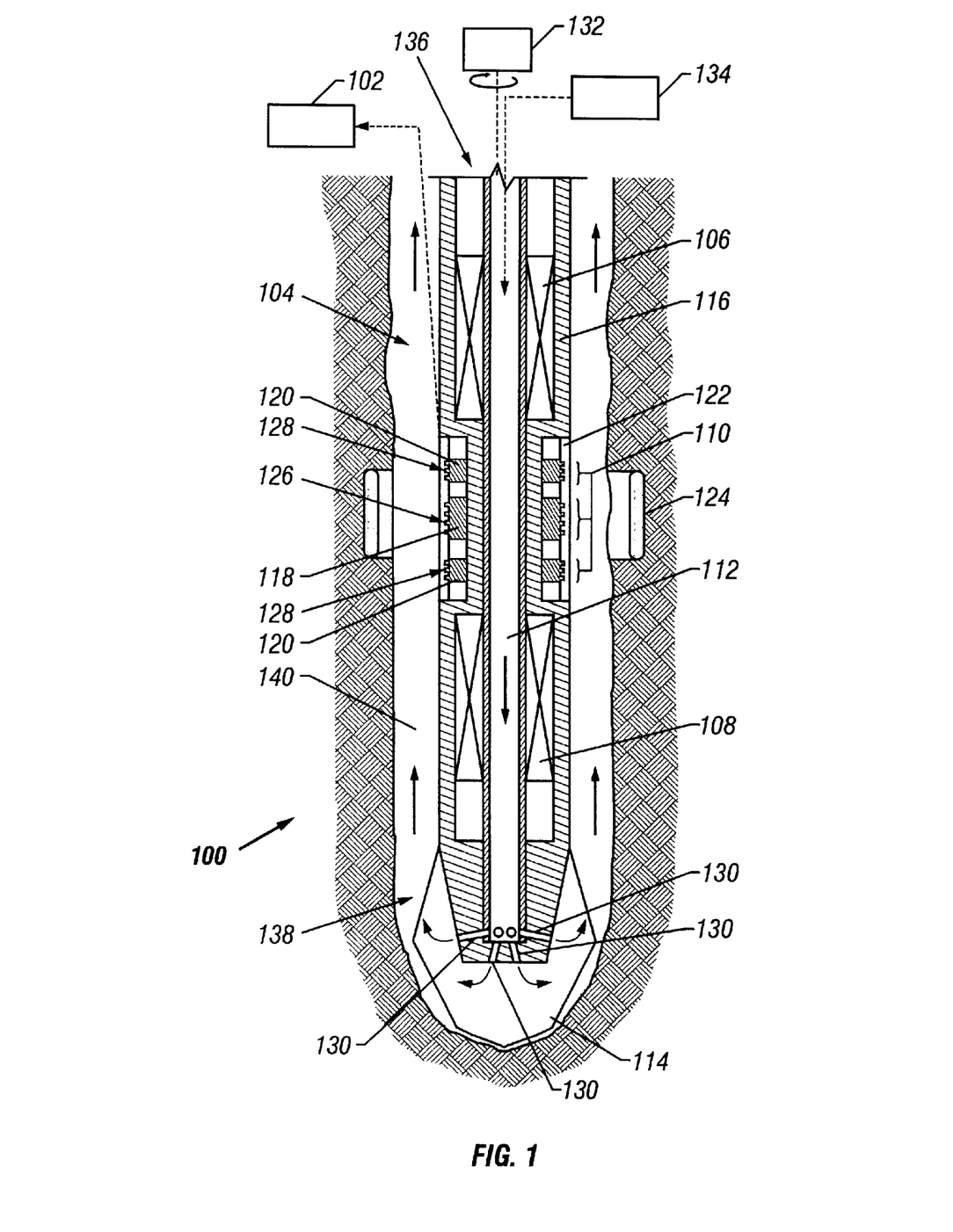
FIG. 1 is a schematic cross-section of an NMR tool system disposed in a well.

FIG. 1 is a schematic cross-section of a NMR LWD system generally known in the art, but modified and improved as not previously known in the art. A drilling system 100 includes a drill string 136 carried by a jointed drill pipe or coiled tubing. The drill string 136 has a bottom hole assembly (BHA) 104, the distal end of which carries a drill bit 114 for drilling a borehole 138 from the Earth's surface into a subterranean formation in order to reach production reservoirs contained therein. The drill bit 114 is rotated typically by turning the drill pipe with a surface motor 132 or by a downhole mud-driven motor (not shown) or by both. The drill string has a central bore 112 for conveying drilling mud to the drill bit 114. As indicated by arrows on FIG. 1, the mud exits the drill string 136 through multiple ports 130 and returns to the surface via the annular region (annulus) 140 between the drill string and the wall of the borehole 138. At the surface, the mud is cleaned and circulated back to the drill string under pressure by any suitable circulation system 134 known in the art.

The BHA 104 includes a NMR measurement tool for determining at least one parameter of interest of formation fluids trapped within the subterranean formation. As with standard tools known in the art, the NMR system of the present invention includes one or more magnets 106 and 108 having substantially time-invariant (static) magnetic fields, which extend into the formation. These magnets are typically permanent magnets or electromagnets and have polar ends usually designated by the terms North (N) and South (S). The magnets 106 and 108 are polarized and oriented with opposing magnetic fields by having the like-poles toward a center plane between the two magnets. This orientation creates a strong static magnetic field in a volume of examinations beyond the borehole and mudcake. The static magnetic field may be substantially homogeneous within the volume, or the field may be a gradient field within the volume.

An RF antenna section 110 is located between magnets 106 and 108. The antenna 110 includes a field-forming solenoid group of RF transmission and receiving windings 126 helically disposed around a core 118 preferably selected from a soft ferrite material. In some NMR tool configurations, the antenna 110 may also include transmission and receiving coupling control windings 128 helically disposed around dedicated cores 120. The antenna 110 is constructed and tuned, the details of which will be described later with respect to FIG. 3, such that a magnetic field is generated and extends into the formation. At a distance beyond the mud-cake and invasion region of the borehole, the coplanar fields of the DC magnets 106 and 108 is substantially homogeneous and the field generated by the antenna 110 have a substantially perpendicular intersection in a volume 124 known as the measurement volume, the zone of sensitivity or the volume of examination.

The instrument antenna 110 is protected from downhole environmental damage such as impact by rock cuttings flowing to the surface in the annulus 140 by a not-shown and non-conductive materials and a non-conductive wear plate 122 typically selected from a hard, temperature resistant material such as a ceramic.

Figure 5:
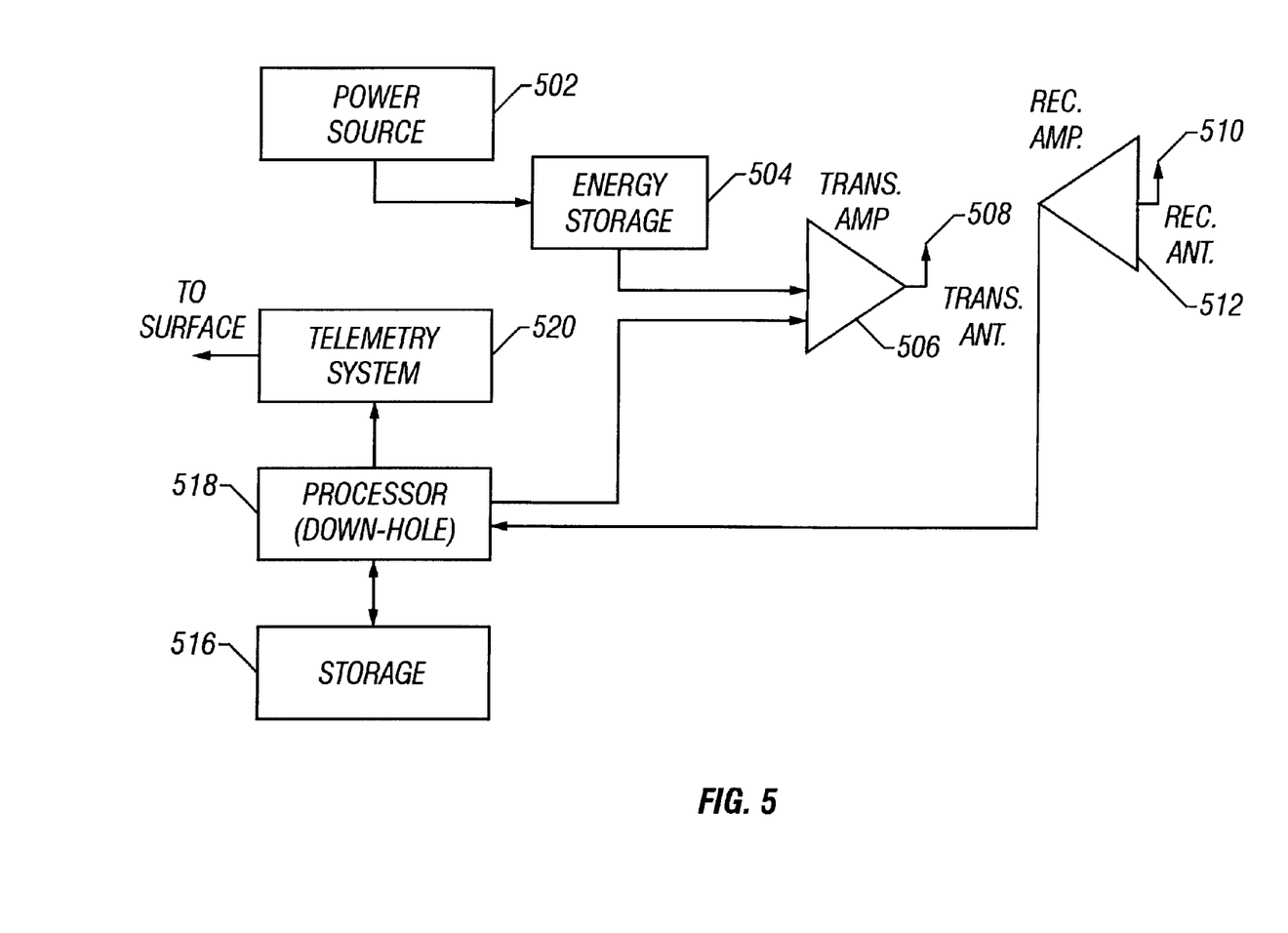
FIG. 5 is a system schematic of the downhole electronics according to the present invention.

Referring to FIGS. 1 and 5, other features include a downhole power source 502, energy storage devices 504, a transmission amplifier 506, receiving amplifiers 512 for increasing small NMR echoes received by a receiving antenna 510, a processor 518 for converting the echoes and processing the data, downhole memory capability 516 (usually necessary when mud-pulse telemetry is used, a telemetry system 520 for sending the processed data to a surface controller 102. The system can also be used in wireline applications as depicted in FIG. 2.

Figure 2:
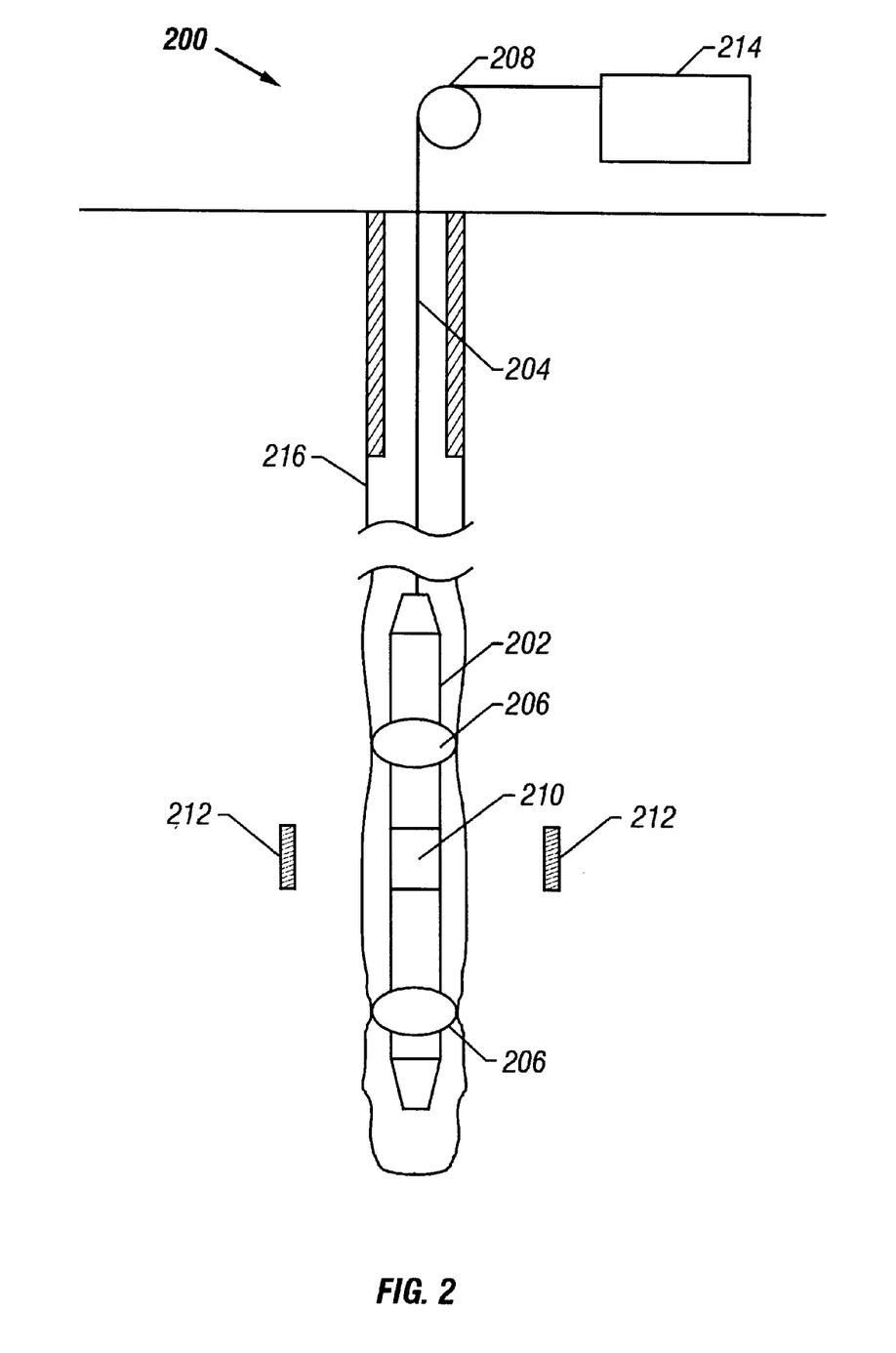
FIG. 2 is a schematic cross-section of an NMR logging tool system disposed in a well on a wireline.

FIG. 2 shows a wireline embodiment of the present invention. In a typical wireline measuring system 200, a plurality of measurement sensors and a control unit is conveyed into a borehole 216 for measuring parameters of interest downhole by a well logging cable 204. The instrument housing 202 includes at least one but preferably at least two well engaging pad members 206 for providing stability for the sensors. The housing 202 includes the NMR tool 210 which is described above with respect to FIG. 1. The antenna portion of the NMR tool 210 is preferably disposed in the housing 202 between pad members 206. When the RF antenna coils are activated, a zone of sensitivity 212 is created beyond the mudcake and invasion zone of the borehole 216. A surface hoist 208 controls the position of the housing 202 and attached NMR tool 210 in a conventional manner known in the art. Data acquired and processed downhole is sent to a surface controller 214 that includes a processor and output or storage device.

The portion of the present invention described thus far is the known NMR system. The present invention to be further described hereinafter is an improvement over all prior art in that the present invention can significantly reduce noise when practiced with any configuration of an NMR system utilizing transmission and receiving antennas with core material subject to dimensional distortion in the presence of a magnetic field. For example, the configuration just described includes multiple core sections. The present invention may also be practiced with a single core section, around which are disposed transmission and receiving windings.

Figure 3:
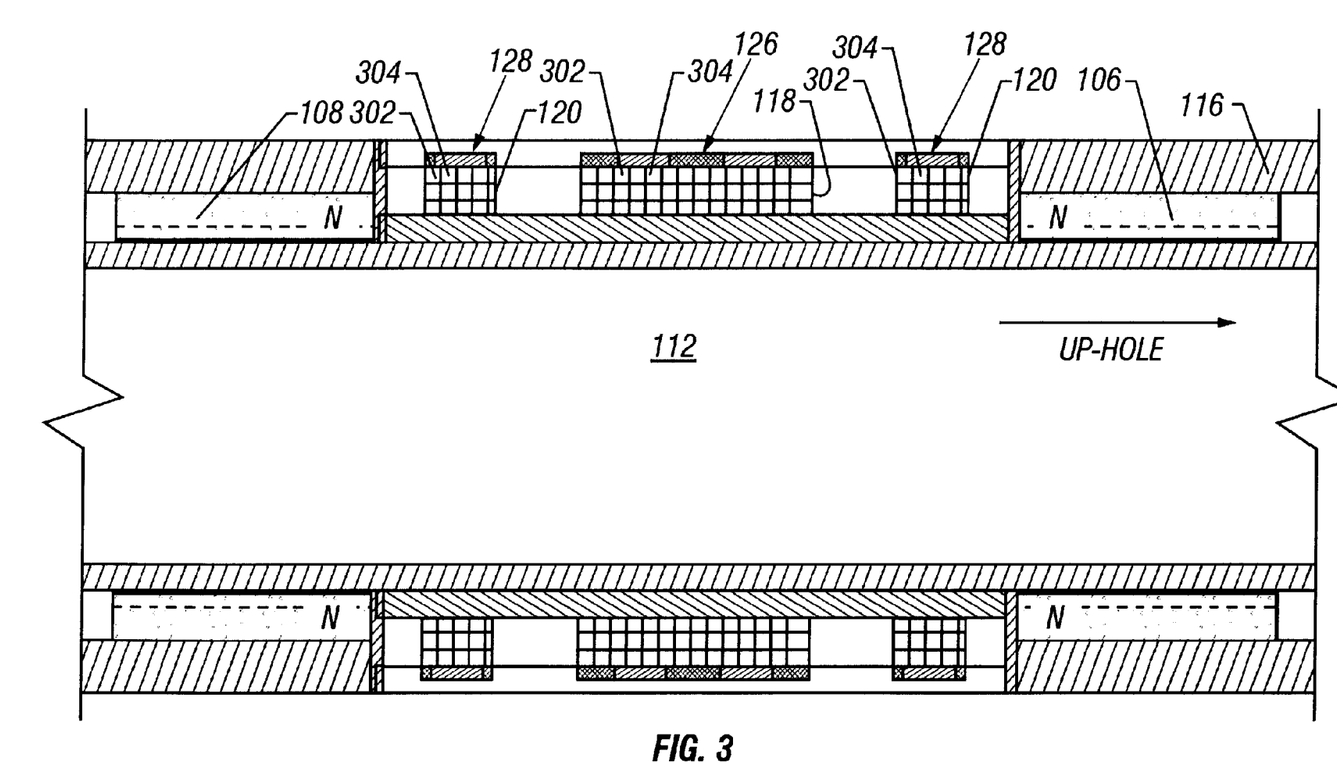
FIG. 3 is a cross-sectional view through an axial plane of the NMR tool shown in FIG. 1.

FIG. 3 is a cross sectional view of the antenna portion of the LWD embodiment from FIG. 1 further showing the ferrite core members in a matrix configuration according to the present invention. The RF antenna section 110 (see FIG. 1) is located between magnets 106 and 108. The tool is shown disposed in the BHA collar 116 (see FIG. 1). RF transmission and receiving windings 126 are helically disposed around a core 118 shown as a matrix. Also shown are coupling control windings 128 helically disposed around dedicated cores 120 also in matrix form. Each matrix comprises a plurality of polygonal cylindrical tiles 302 and 304. The tiles are selected such that some exhibit expansion magnetostrictive characteristics in at least one selected direction, which will be referred herein as positive (+) tiles 304. Other tiles are selected from materials that exhibit contractive magnetostrictive characteristics in at least one selected direction. These tiles will be referred herein as negative (−) tiles 302.

Any suitable complementary magnetostrictive materials may be used to construct the positive and negative tiles. For example, experiments show Ferrite K250 from the vendor Kaschke has a negative magnetostriction and Ferrites F47 and F44 from vendor NMG-Neosid show positive magnetostriction. The F47 and F44 Ferrites are Manganese Zink Ferrites, and the K250 is a Nickel Ferrite. In the preferred embodiment, the core sections are constructed with tiles formed from Ferrite into "bricks" as shown in FIG. 3. The bricks are arranged to form a complete hollow core cylinder (i.e. no ribs in the Ferrite).

In order to utilize the effect of compensating the magnetostrictive effect mix Ferrites may also be mixed with other materials (such as metals) having different magnetostrictive properties. It may also be advantageous to mix a relatively large amount of Ferrites with a smaller amount of materials with giant magnetostrictive effect (such as Terfenol) having opposite direction of magnetostriction. The materials can be mixed in small bricks or other particles as long as the direction of magnetostriction is taken into account. Care should be taken when choosing a material to mix with the Ferrites. When using a metal additive for example, as little metallic material as possible should be used to mix with the Ferrites. Otherwise, the magnetic properties of the ferrites may be adversely affected beyond usefulness as an antenna core.

For the purposes of this application, the term negative magnetostriction is defined as a material that exhibits contractive magnetostrictive characteristics in at least one selected direction, and positive magnetostriction is defined as a material that exhibits expansion magnetostrictive characteristics in at least one selected direction.

FIG. 4 is a representation of several polygonal cross-sections (FIGS. 4A–4D) of tiles combined in matrices. Any matrix formation is acceptable to as long as the placing of positive tiles 304 and negative tiles 302 creates and alternating pattern in the matrix. Each tile is a polygonal cylinder with any desired number of perimeter sides. Two end surfaces of each tile may be substantially planar or contoured in order to provide any desired matrix shape.

Figure 4A:
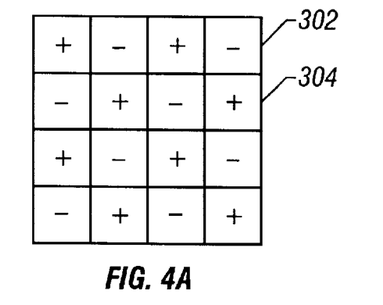
FIG. 4 is a set of FIGS. 4A through 4E showing multiple configurations of positive and negative tile matrices.
Figure 4B:
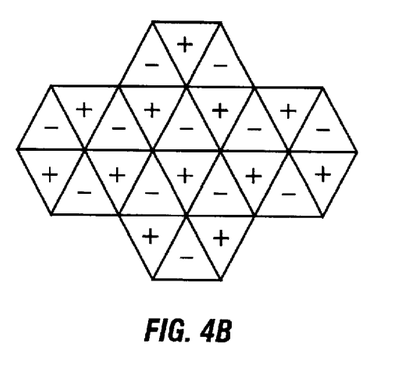
Figure 4C:
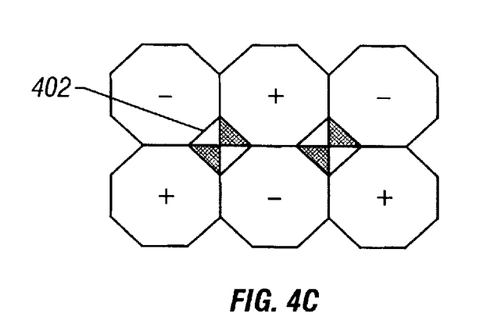
Figure 4D:
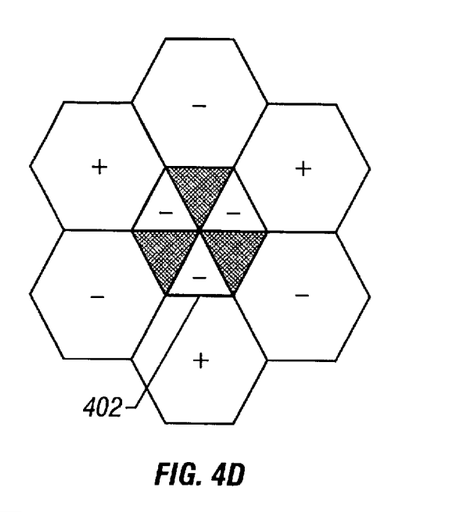
Figure 4E:
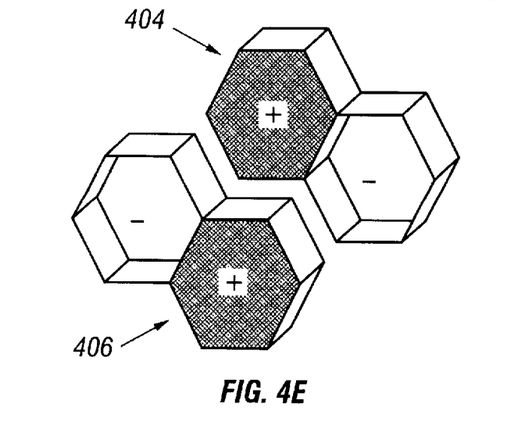

FIG. 4E shows polygonal cylinders in a multi-layer format. Each layer 404 and 406 is comprised of a matrix with alternating tiles as described above. Likewise, each tile in one layer 404 is selected and placed to oppose the magnetostrictive motion of the adjacent layer 406 or layers.

FIGS. 4C and 4D show the preferred selection and placement of positive 304 and negative 302 tiles in cases where a core section 402 of the tile matrix must have a different cross section that the surrounding tiles. It is also possible to have the core section 402 made from a suitable material exhibiting substantially no magnetostrictive characteristics in order to simplify the manufacturing process. The magnetostrictive characteristics are typically multi-directional in nature. The tiles should be selected, shaped and arranged for optimum magnetostrictive cancellation based on the choice of tool configuration.

FIG. 5 is a system flow of the downhole electronics portion of the present invention. The magnets creating a substantially DC field is not shown. The electronics may be housed in a plurality of recesses or pockets and sealed to protect the components from environmental damage. The components may be placed above or below the sensor elements. Preferably, the amplifiers 506 and 512 are placed as near as possible to the respective transmit and receive antenna could 508 and 510. Improper placement may result in noise other than magnetostrictive ringing. The main components required for NMR operation are a RF transmitter amplifier 506, to drive a transmit antenna 508, a low noise receiver pre-amplifier 512 connected to the receiving antenna 510, a downhole processor 518 to schedule pulses, detect echoes, and to analyze and compress the data and to control the tool, an electronic memory device 516 for data storage, and a telemetry system 520 to send the data to the surface. The telemetry system 520 may be mud pulse for LWD and MWD applications, or it may be by conductor for wireline applications. The power source 502 for the electronics is typically a turbine generator driven by mudflow coupled to an energy storage device 504 that stores energy to increase the available power to the sensor.

Other magnetic resonance applications outside the well logging field wherein compensation for magnetostrictive ringing is desirable are considered within the scope of this invention. For example, certain medical applications use magnetic resonance. In these applications the volume of examination is typically within a patient. The permanent magnets and antennas are disposed such that the static and RF fields are directed into the patient. The medical apparatus used may be improved by using an antenna according to this invention.

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

What is claimed is:

1. A nuclear magnetic resonance tool for analyzing a volume of examination in a material comprising:
   (a) a magnet for inducing a static magnetic field in the volume of examination;
   (b) an antenna for transmitting a radio frequency magnetic field substantially perpendicular to the static magnetic field in the volume of examination, the antenna having a core including a first portion having positive magnetostriction in the presence of the radio frequency magnetic field, and a second portion having negative magnetostriction in the presence of the radio frequency magnetic field; and
   (c) a receiver for sensing a signal emitted from the material.

2. The nuclear magnetic resonance tool of claim 1 wherein the volume of examination includes a subterranean formation with a fluid therein.

3. The nuclear magnetic resonance tool of claim 1 wherein the static magnetic field is selected from a group consisting of (i) a substantially homogeneous field within the volume of examination and (ii) a gradient field within the volume of examination.

4. The nuclear magnetic resonance tool of claim 1 wherein the first portion further comprises a first at least one polygonal cylinder shape comprising a first ferrite powder fixed in a first epoxy, and the second portion further comprises a second at least one polygonal cylinder shape comprising a second ferrite powder fixed in a second epoxy.

5. The nuclear magnetic resonance tool of claim 1 wherein the first portion is arranged in a first plurality of tiles and the second portion is arranged in a second plurality of tiles.

6. The nuclear magnetic resonance tool of claim 5 wherein the first plurality of tiles and second plurality of tiles are polygonal cylinders.

7. The nuclear magnetic resonance tool of claim 5 wherein the first plurality of tiles and second plurality of tiles are geometrically arranged in an alternating fashion such that positive tiles are adjacent negative tiles.

8. The nuclear magnetic resonance tool of claim 7 wherein the geometric arrangement created by tiles having a cross-sectional area selected from a group consisting of (i) square positive and square negative tiles, (ii) triangular positive and triangular negative tiles, (iii) hexagonal positive and hexagonal negative tiles surrounding triangular positive and triangular negative tiles, and (iv) octagonal positive and octagonal negative tiles surrounding triangular positive and triangular negative tiles.

9. The nuclear magnetic resonance tool of claim 1 wherein the first portion and second portion are coupled to form at least one layer of the core.

10. The nuclear magnetic resonance tool of claim 9 wherein the at least one layer is at least two layers.

11. The nuclear magnetic resonance tool of claim 1 further comprising a member for conveying the tool into a well, the member selected from the group consisting of (i) a rotatable drill string, (ii) a coiled tube and (iii) a wireline.

12. The nuclear magnetic tool of claim 1 wherein the signal is indicative of at least one parameter of interest of the material.

13. The nuclear magnetic tool of claim 1 wherein the receiver is a second antenna having a core including a first portion having positive magnetostriction in the presence of a second radio frequency magnetic field, and a second portion having negative magnetostriction in the presence of the second radio frequency magnetic field, the second radio frequency magnetic field being created by the signal flowing through an inductive winding of the second antenna.

14. An antenna with reduced magnetostrictive noise, the antenna comprising:
   (a) at least one inductive winding; and
   (b) a core including a first portion having positive magnetostriction in the presence of a radio frequency magnetic field, and a second portion having negative magnetostriction in the presence of the radio frequency magnetic field.

15. A method for analyzing a volume of examination in a material using a nuclear magnetic resonance tool, the method comprising:
   (a) using a magnet to produce a static magnetic field in the volume of examination;
   (b) using an antenna to transmit a radio frequency magnetic field substantially perpendicular to the static magnetic field, the antenna having a core including a first portion having positive magnetostriction in the presence of the radio frequency magnetic field, and a second portion having negative magnetostriction in the presence of the radio frequency magnetic field; and
   (c) sensing a signal emitted from the material with a receiver.

16. The method of claim 15 wherein the material is a subterranean formation with a fluid therein.

17. The method of claim 15 wherein the static magnetic field within the volume is selected from a group consisting of (i) a substantially homogeneous field and (ii) a gradient field.

18. The method of claim 15 wherein (b) further comprises constructing the first portion using a first at least one polygonal cylinder shape comprising a first ferrite powder fixed in a first epoxy, and constructing the second portion using a second at least one polygonal cylinder shape comprising a second ferrite powder fixed in a second epoxy.

19. The method of claim 15 wherein the first portion is arranged in a first plurality of tiles and the second portion is arranged in a second plurality of tiles.

20. The method of claim 19 wherein the first plurality of tiles and second plurality of tiles are polygonal cylinders.

21. The method of claim 19 further comprising arranging the first plurality of tiles and second plurality of tiles are geometrically in an alternating fashion such that the first plurality of tiles are adjacent the second plurality of tiles.

22. The method of claim 21 wherein the geometric arrangement is created using tiles having a cross-sectional area selected from a group consisting of (i) square positive and square negative tiles, (ii) triangular positive and triangular negative tiles, (iii) hexagonal positive and hexagonal negative tiles surrounding triangular positive and triangular negative tiles, and (iv) octagonal positive and octagonal negative tiles surrounding triangular positive and triangular negative tiles.

23. The method of claim 15 wherein the first and second portions are coupled to form at least one layer of the core.

24. The method of claim 23 wherein the at least one layer is at least two layers.

25. The method of claim 15 further comprising conveying the tool into a well with a member selected from the group consisting of (i) a rotatable drill string, (ii) a coiled tube and (iii) a wireline.

26. The method of claim 15 further comprising processing the signal to obtain at least one parameter of interest of the material.

27. A nuclear magnetic resonance LWD apparatus for analyzing in-situ a formation containing a fluid in a volume of examination to determine at least one parameter of interest of the formation, the apparatus comprising:

(a) a magnet for inducing a static magnetic in the volume of examination;

(b) an antenna for transmitting a radio frequency magnetic field into the volume of examination substantially perpendicular to the static magnetic field, the antenna having a core including a first portion having positive magnetostriction in the presence of the radio frequency magnetic field, and a second portion having negative magnetostriction in the presence of the radio frequency magnetic field;

(c) a controller for controlling the transmission of the radio frequency magnetic field;

(d) a receiving antenna for sensing a signal emitted from the formation indicative of the at least one parameter of interest;

(e) a downhole processor for processing the signal to obtain the at least one parameter of interest;

(g) a telemetry system for transmitting the parameter of interest to the surface of the well; and (h) a surface controller for receiving the parameter of interest, the surface controller further comprising a receiver, a processor, and an output device.

* * * * *